(12) United States Patent
Ju et al.

(10) Patent No.: US 7,691,296 B2
(45) Date of Patent: Apr. 6, 2010

(54) METHOD FOR STABILIZING ACTIVE COMPONENTS USING POLYOL/POLYMER MICROCAPSULE, AND COSMETIC COMPOSITION CONTAINING THE MICROCAPSULE

(75) Inventors: Hee Kyung Ju, Seoul (KR); Jin Woong Kim, Kyunggi-do (KR); So Mi Lee, Kyunggi-do (KR); Sang Hoon Han, Kyunggi-do (KR); Ih Seop Chang, Kyunggi-do (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 10/716,877

(22) Filed: Nov. 20, 2003

(65) Prior Publication Data

US 2004/0108608 A1 Jun. 10, 2004

(30) Foreign Application Priority Data

Nov. 25, 2002 (KR) .................. 10-2002-0073433
Mar. 28, 2003 (KR) .................. 10-2003-0019384

(51) Int. Cl.
*B01J 13/02* (2006.01)
*B01J 13/06* (2006.01)
*A61K 9/58* (2006.01)
*A61K 8/11* (2006.01)

(52) U.S. Cl. ................ 264/4.32; 264/4.33; 428/402.2; 424/491; 424/497

(58) Field of Classification Search ............... 252/316; 428/402–402.24; 424/491, 497; 427/213.3–213.36; 264/4–4.7
See application file for complete search history.

(56) References Cited

U.S. PATENT DOCUMENTS

| | | | |
|---|---|---|---|
| 3,664,963 A | * | 5/1972 | Pasin .................... 427/213.36 |
| 3,891,570 A | * | 6/1975 | Fukushima et al. .... 427/213.36 |
| 4,389,330 A | | 6/1983 | Tice et al. |
| 4,898,781 A | * | 2/1990 | Onouchi et al. ........ 428/402.22 |
| 5,385,959 A | | 1/1995 | Tsaur et al. |
| 5,407,609 A | | 4/1995 | Tice et al. |
| 5,460,817 A | | 10/1995 | Chamberlain et al. |
| 5,672,213 A | * | 9/1997 | Asgharian et al. ............. 134/42 |
| 5,688,891 A | * | 11/1997 | Hovestadt et al. ............. 528/73 |
| 5,911,923 A | | 6/1999 | Hart et al. |
| 6,420,333 B1 | | 7/2002 | Neuser et al. |
| 2001/0014339 A1 | | 8/2001 | Shigeyuki et al. |

FOREIGN PATENT DOCUMENTS

| | | |
|---|---|---|
| JP | A 1982-093912 | 6/1982 |
| JP | A 1999-505464 | 5/1999 |
| WO | WO 96/03039 | 2/1996 |
| WO | WO 00 32307 A | 6/2000 |

OTHER PUBLICATIONS

Official Action mailed Oct. 22, 2007 in the counterpart European application.
Japanese Official Action in SN 10-2003-394525 and English translation, Oct. 23, 2009.
Korean Official Action in SN 10-2003-0019384 and English translation dated Oct. 15, 2009.

* cited by examiner

*Primary Examiner*—James Seidleck
*Assistant Examiner*—Saira Haider
(74) *Attorney, Agent, or Firm*—Nixon & Vanderhye P.C.

(57) ABSTRACT

The present invention relates to a method for stabilizing enzyme and water- and oil-soluble active components using polyol/polymer microcapsules, and to a cosmetic composition containing the enzyme and the microcapsules. More particularly, the present invention relates to polyol/polymer microcapsules which effectively stabilize the enzyme and active components, which are unstable in the formulations, through increasing the solubility thereof in hydrophobic polymer by using polyol, and to a method for preparing the polyol/polymer microcapsules.

4 Claims, 2 Drawing Sheets

METHOD FOR STABILIZING ACTIVE COMPONENTS USING POLYOL/POLYMER MICROCAPSULE, AND COSMETIC COMPOSITION CONTAINING THE MICROCAPSULE

FIELD OF THE INVENTION

The present invention relates to a method for stabilizing enzyme and water- and oil-soluble active components using polyol/polymer microcapsules, and to a cosmetic composition containing the enzyme and the microcapsules. More particularly, the present invention relates to polyol/polymer microcapsules that effectively stabilize the enzyme and active components, which are unstable in the formulations, through increasing the solubility thereof in hydrophobic polymer by using polyol, and to a method for preparing the polyol/polymer microcapsules.

BACKGROUND OF THE INVENTION

Together with the developments of bio-industry, various enzymes have been used as therapeutic or healing agents. However, because most of enzymes are denatured before doing useful operation due to their very short half-life, application of the enzymes has been restricted by their low stability. Recently, the establishment of transfer systems to increase the application of the enzyme has been studied. Among many enzyme transfer systems, a transfer system using biodegradable polymer as the wall material of the microcapsules has many merits in the aspect of long-term injection (Y. Okawa, M. Yamamoto, H. Okada, T. Yashiki, T. Shimamoto, *Chem. Pharmac. Bull.,* 1988, 5, 1095; H. Okada, Y. Doken, Y. Ogawa, H. Toguchi, *Pharmac. Res.,* 1994, 11, 1143). However, this transfer system also requires stability for a long time storage. Generally, water-oil-water multi-emulsion systems are used to make a microcapsules containing enzymes, but the enzyme activity is decreased on the interface of water-oil (P. Couvreur, M. J. Blanco-Proeto, F. Puisieux, B. Ropues, E. Fattal, *Adv. Drug Del. Rev.,* 1997, 28, 85; H. Sah, *J. Pharmac. Sci.,* 1999, 88, 1320). Therefore, recently a solid-oil-water emulsion system has been used because the solid-oil-water emulsion maintains enzyme activity in the solid (T. Morita, Y. Sakamura, Y. Horikiri, T. Suzuki, H. Yoshino, *J. Control. Rel.,* 2000, 69, 435). However, these systems have problems that lots of the enzymes capsulized in the solid-oil-water emulsion becomes denatured because of heat and physical strength received during manufacturing process.

Alternatively, various active components of a cosmetic composition have excellent effects such as improving wrinkling of the skin, whitening effect, reinforcing moisturization and antioxidation, but their application has been restricted because they are easily deteriorated through contact with external stimulants such as air or moisture, for example, discoloration, change of scent or the like. Therefore, stabilization of the enzyme is actively studied.

To solve such a problem, active components have been capsulized to be blocked it from external stimulation. Polymers have been mainly employed to capsulize the active components. Methods for capsulizing the active components using polymers include interfacial polycondensation, spray dry, coacervation, solvent evaporation or the like. Using such methods, an oil-soluble component is generally collected in hydrophobic polymer and a water-soluble component is generally collected in hydrophilic polymer. To improve stability of a water-soluble component, Jeffery et al. suggested double emulsion-solvent evaporation techniques (1993). This method capsulizes a water-soluble component more stably than simple w/o emulsion-solvent evaporation techniques, but it has a low collection rate because the water-soluble component is diffused into an aqueous media. Remunan-Lopez et al. suggested a multinuclei microcapsule that capsulizes oil- and water-soluble components at the same time by using chitosan (Eur. J. Pharma. Biopharma., 1998, 45, p.49). This method uses modified w/o/w-solvent evaporation techniques, however the microcapsules can be produced only when the following preconditions are satisfied: an inside aqueous phase should be viscous, an active component to be contained should be dispersed and perfectly dissolved in a concentrated solution of chitosan, an organic phase should be polymer dilute solution, and the organic solvent and the polymer should not be activated with chitosan.

A method for simultaneously capsulizing oil- and water-soluble components in liposome (not polymer) is disclosed in Korean Patent Publication No. 1993-211990. The liposome has a merit of capsulizing an oil- and a water-soluble component at the same time, however the stability of liposome in a cosmetic formulation has not yet been verified

SUMMARY OF THE INVENTION

The inventors of the present invention made an effort to invent a stabilized transfer system that increases the solubility of an active component without changing the physical properties of a polymer, and can block denaturation of an enzyme. As a result, the inventors discovered that a polyol/polymer microcapsule is suitable to stabilize an enzyme and an active component, and completed the present invention.

Therefore, the object of the present invention is to provide a polyol/polymer microcapsule which can stabilize at least one of the oil- and water-soluble components in the microcapsule.

Another object of the present invention is to provide a polyol/polymer microcapsule which can stably contain an enzyme using a low-molecular and a high-molecular weight polyol and polymer solution, and provides a method for preparing the microcapsule.

In addition, the present invention provides a cosmetic composition containing the polyol/polymer microcapsule in order to maintain efficacy of an active component and an enzyme for a long time.

DETAILED EXPLANATION OF THE INVENTION

Figure 1:
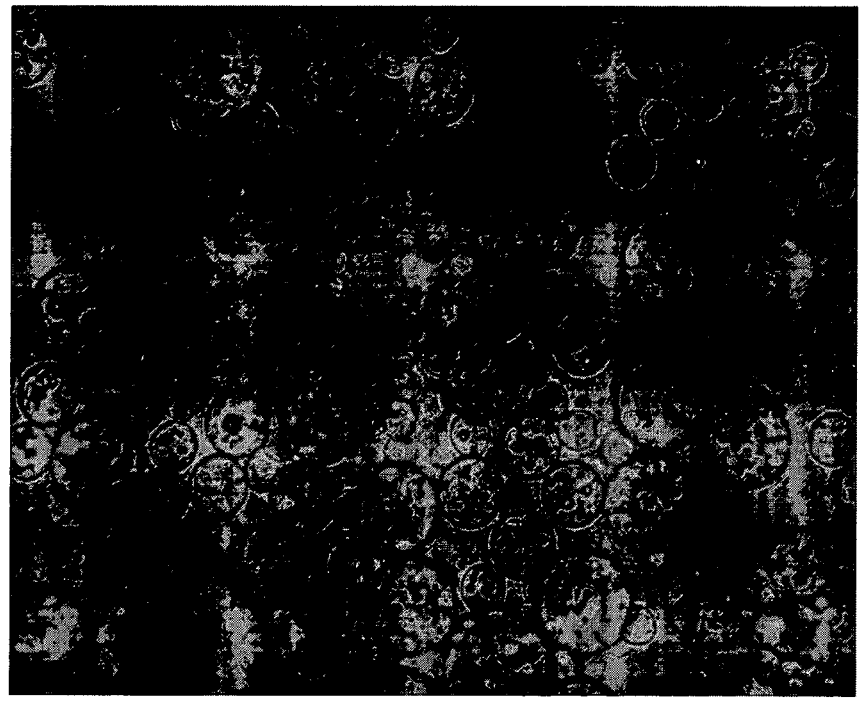
FIG. 1. shows an optical microscopic photograph of polyethyleneglycol (400 g/mol)/polycaprolactone (8000 g/mol) microcapsules.

The present invention provides a polyol/polymer microcapsule stably containing an enzyme using a low-molecular and a high-molecular weight polyol and polymer solution, and a method for preparing the microcapsule.

A method for preparing polyol/polymer microcapsules according to the present invention comprises the following steps of:

1) dissolving a mixture of low- and a high-molecular weight polyols in polymer solution to make polyol solution;
2) adding the polyol solution into an aqueous solution containing stabilization agent to emulsify;
3) removing solvent from the emulsion of step 2) while stirring under reduced-pressure condition in a vacuum evaporator to make dispersed solution;
4) filtering the dispersed solution to remove aqueous materials in order to collect microcapsules; and
5) drying the collected microcapsules in a vacuum evaporator at room temperature to obtain polyol/polymer microcapsules.

Preferably, the polymer solution of step 1) may contain wall-component polymer for microcapsule. In more detail, the low and the high molecular weight polyol are mixed, and the mixture is dissolved in a polymer solution prepared by dissolving wall-component polymer in a solvent. The amount of the sum of low molecular weight polyol and high molecular weight polyol and the amount of wall-component polymer contained in the polymer solution may be controlled according to the thickness of the wall material, and preferably the same. In addition, the mixture of polyols and the wall-component polymer are respectively employed in about 20 wt % to the solvent.

The resulting solution is poured into an aqueous solution containing a stabilizer and emulsified by a homogenizer.

The resulting emulsion is stirred in a vacuum evaporator under reduced-pressure for 10~120 min. to remove solvent. The resultant is then filtered to collect microcapsules and to remove other aqueous material. The collected microcapsules are completely dried in a vacuum dryer while blocking light at room temperature for 24~48 hours.

In addition, the present invention provides a microcapsule containing not only oil- but also water-soluble active components produced by using amphiphilic polyol, and provides a cosmetic composition containing the microcapsule.

Especially, the cosmetic composition of the present invention can contain such active components as licorice and ascorbic acid that have been restricted in their use in cosmetic compositions due to their decreased stability and discoloration through contact with high temperatures, moisture or air, because the microcapsule can prevent a reduction of the efficiency of the active component by collecting the active component in the polyol/polymer microcapsule.

A method for preparing microcapsules containing an active component according to the present invention may comprise the following steps of:

1) dissolving at least one active components selected from an oil- and a water-soluble active components in a solution of a polyol in a solvent;
2) dispersing the mixture of step 1) in a polymer solution, then emulsifying to collect an emulsion; and
3) removing the polyol and the solvent from the emulsion to collect a hard polymer microcapsules.

To explain the preparation method in more detail, preferably, polyol is dissolved in a solvent at a mixing ratio of polyol to solvent of 0.05:1~1:1, then the oil- and water-soluble active components are added to the resulting solution.

The mixed solution is added to the polymer solution, stirred and dispersed by a magnetic stirrer, and emulsified at room temperature for 5 min, at 5,000 rpm to collect an emulsion.

The polyol and the solvent are removed from the emulsion while stirring under reduced-pressure, then a hard polyol/polymer microcapsules are produced.

When unstable active components are stabilized by using the polymer microcapsule, generally an oil-soluble component is collected in a hydrophobic polymer and a water-soluble component is collected in a hydrophilic polymer. It is difficult to collect an oil- and a water-soluble component in a polymer at the same time. However, the microcapsules according to the present invention can stably collect an oil- and a water-soluble component at the same time through a simple manufacturing process using polyol when preparing the microcapsules.

To collect an active component into the polymer, the active component is dissolved or completely dispersed in a solvent. The present invention manifolds the active component that is able to be collected into the polymer by using amphiphilic polymer. Active components which can be collected into the polyol/polymer microcapsule of the present invention include those able to dissolve in polyol, polymer solvent, or a mixing solution of polyol and polymer; for example, oil-soluble active components including retinol, retinyl acetate, retinyl palmitate, tocopherol, tocopheryl acetate, tocopheryl linoleate, tocopheryl nicotinate, linoleic acid, coenzyme Q-10, resveratrol, lipoic acid and licorice extract; water-soluble active components including ascorbic acid and derivatives thereof, and chlorogenic acid. The present invention may employ one or more of the above active components.

The polyol used in the present invention increases the solubility of the active component and stabilizes the active component by forming a polyol domain in the microcapsule. The polyol includes polyethylene glycol, polypropylene glycol, and copolymers and derivatives thereof; and compounds comprising low molecular weight alcohol, such as butylenes glycol, propylene glycol or glycerin. The amount of the polyol is preferably about 0.1~70 wt % to the total polymer weight. If the amount of the polyol is less than 0.1 wt %, the active component is difficult to disperse efficiently and if the content of the polyol is more than 70 wt %, the yield of the microcapsule decreases.

Moreover, the polyol/polymer microcapsules produced by the above method can be applied to stabilize an enzyme or a protein. Further, the techniques can be introduced other enzyme utility techniques.

For example, a polyol/polymer microcapsule containing an enzyme according to the present invention may have a triple-layered constitution, in which the enzyme forms the internal nuclei, hydrophobic high molecular weight polyol surrounds the enzyme, and finally the wall-component polymer forms the outer wall.

A method for manufacturing a triple-layered microcapsule to stabilize an enzyme comprises the following steps of:

1) dispersing an enzyme into a low molecular weight polyol;
2) dispersing the solution of stabilized enzyme/polyol obtained in step 1) into a polymer solution containing high molecular weight polyol dissolved therein, then emulsifying the solution to collect emulsion; and
3) solidifying the enzyme/polyol/polymer solution obtained in step 2) to collect a hard polymer microcapsules.

The method for preparing microcapsules according to the present invention will hereunder be described in more detail.

The enzyme is dispersed into a low molecular weight polyol. Generally, an enzyme has partial solubility in a low molecular weight polyol. In this case, an enzyme forms spherical dispersoids with relatively high wettability in a low molecular weight polyol and only the external layer of the enzyme partially dissolves therein to form enzyme/polyol mixture phase dispersed solution. The enzyme/polyol dispersed solution is then re-dispersed into a polymer solution, which comprises a high molecular weight polyol, a wall-component polymer (wall material) and a solvent. The enzyme phase protected with a low molecular weight polyol through the above process can stably disperse without being affected by solvent in the polymer solution.

The high molecular weight polyol acts as a buffer that prevents direct contact between the enzyme and the hydrophobic polymer wall material in the microcapsule.

After that, the solvent is selectively removed from the resulting solution of enzyme/polyol/polymer/solvent. By the removal of the solvent, phase separation is formed because the polyol is immiscible in the polymer. During this separation, the aqueous low molecular weight polyol flows out to the outer aqueous phase through external interface of the microcapsule, due to its high polarity, and high molecular weight polyol remains in the microcapsule. Accordingly, the microcapsule is composed of triple layers in which the enzyme forms the internal nuclei, hydrophobic high molecular weight polyol surrounds the enzyme, and finally the wall-component polymer forms the outer wall.

To maintain the characteristics of the enzyme and to block fundamentally undesirable contact with external stimulation, the microcapsules according to the present invention used low molecular weight polyol as the template for forming the internal vesicle of the microcapsule and as the dispersion media of the enzyme, and used high molecular weight polyol as the hydrophobic dispersing agent of the enzyme and as the blocking agent to prevent the enzyme from being denatured by the polymer of the internal wall material, which is totally different from conventional simple microcapsule, and can maintain stability of the enzyme during the formulation process and long time of storage.

In addition, it is expected that the microcapsules of the present invention may be applied to pharmaceuticals or cosmetics.

Enzymes used in the present invention include oxidoreductase such as glucose oxidase, xanthine oxidase and D-amino acid oxidase; transferase such as transaminase and hexokinase; hydrolase such as lipase, amylase, pepsin, trypsin, urease, asparaginase and papain; lyase such as aldolase, fumarase and pectin lyase; isomerase such as lactate catal isomerase, lactate racemase and UDP-d-glucose-4-epimerase; and synthase such as aspartate ammonia lyase and DNA ligase. These enzymes may be employed singly or by mixing.

In the present invention, a mixture of a low and a high molecular weight polyol is employed. The low molecular weight polyol makes the enzyme disperse completely and acts as a template which flows out to the outside of the microcapsule during the process to form the microcapsule. Preferably, the low molecular weight polyol may be 1000 g/mol and less of polyeter type, for example, polyethylene glycol, polypropylene glycol, copolymers or derivatives thereof; or compounds comprising a low molecular alcohol such as butylenes glycol, propylene glycol or glycerin. Preferably, the amount of the low molecular weight polyol is about 0.1~70 wt % to the total weight of the microcapsule. If the amount of the polyol is less than 0.1 wt %, it is difficult to disperse the active component efficiently and if the amount of the polyol is more than 70 wt %, the yield of the microcapsule decreases.

Because the high molecular polymer does not flow out to the outer phase but remains in the microcapsule, the high molecular weight polyol can provide hydrophobic distribution to an enzyme in the microcapsule and can prevent the enzyme from being denatured by the hydrophobic polymer of the wall material.

The hydrophobicity of the polyol increases according to the molecular weight of the polyol. When a high molecular weight polyol is located between enzyme and hydrophobic polymer of the wall material, the enzyme is efficiently protected by the hydrophobic distribution effect. Therefore, the molecular weight of the polyol should be high enough to increase the hydrophobic distribution effect. Preferably high molecular weight polyol may be more than 1000 g/mol of polyeter wax type, for example, polyethylene glycol, polypropylene glycol, copolymers or derivatives thereof. The amount of the polyol is preferably about 0.1~90 wt % to the total weight of the microcapsule. If the amount of the high molecular polyol is less than 0.1 wt %, it is difficult to expect an efficient hydrophobic distribution effect, and if the amount of the high molecular polyol is more than 90 wt %, it is difficult to form a hard microcapsule because of high concentration of polyol.

Polymers for wall material (wall-component polymer) of the microcapsule include biodegradable hydrophobic aliphatic polyester such as poly-L-lactic acid, poly-D,L-glycolic acid, poly-L-lactic acid-co-glycolic acid, poly-D,L-lactic acid-co-glycolic acid, polycaprolactone, polyvalerolactone, polyhydroxybutyrate, polyhydroxyvalerate, polyorthoester, and copolymers produced from monomers thereof. Polymers for wall material of the microcapsule also include unsaturated carboxylic acid such as polystyrene, poly p- or m-methylstyrene, poly p- or m-ethystyrene, poly p- or m-chlorostyrene, poly p- or m-chloromethylstyrene, polystyrene sulfonic acid, poly p-, m- or t-butoxystyrene, polymethyl(meth)acrylate, polyethy(meth)acrylate, polypropyl (meth)acrylate, poly n-butyl(meth)acrylate, polyisobutyl (meth)acrylate, poly t-butyl(meth)acrylate, poly 2-ethylhexyl (meth)acrylate, poly n-octyl(meth)acrylate, polylauryl (meth)acrylate, polystearyl(meth)acrylate, poly 2-hydroxyethyl(meth)acrylate, polyethylene glycol(meth)acrylate, metoxypolyethylene glycol(meth)acrylate, polyglycidyl (meth)acrylate, polydimethylaminoethyl(meth)acrylate, polydiethylaminoethyl(meth)acrylate, polyvinylpropionate, polyvinylbutyrate, polyvinyleter, polyallylbutyleter, polyallylglycidyleter, poly(meth)acrylic acid and polymaleic acid; polyalkyl(meth)acrylamide, poly(meth)acrylonitrile; and mixtures thereof. The amount of the polymer is preferably about 1~99.99 wt % to the total weight of the microcapsule. If the amount of the polymer is less than 1 wt %, it is difficult to form the microcapsule and if the amount of the polymer is more than 99.99 wt %, it is difficult for the enzyme to be expressed due to the lower concentration of the enzyme.

Solvents for the present invention may comprise any compound that has similar solubility to the polymer used, for example, linear alkan such as hexan, heptan, octan, nonan and decan; alcohol with 4~10 carbons such as butanol, linear or branched pentanol, hexanol, heptanol, octanol, nonanol and decanol; alkyl ester with 7 or more of cabons such as n-hexyl acetate, 2-ethylhexyl acetate, methyl oleate, dibutyl sebacate, dibutyl adipate, and 2-butyl carbamate; aliphatic ketone such as methyl isobutyl ketone and isobutyl ketone; aromatic hydrocarbon such as benzene, toluene and o- or p-xylene; and chlorides such as methylene chloride, chloroform and carbon tetrachloride.

Stabilizers for the present invention may comprise any a water-soluble polymer that can improve dispersion stability of the microcapsule in the water-soluble phase, for example, arabic, tragacanth, karaya, larch, ghatti, locust bean, guar, agar, alginate, carrageenan, furcellaran, pectin, gelatin, starch and derivatives thereof; dextran, xanthan gum and derivatives thereof produced by microorganism fermentation synthesis; and copolymer containing polyvinyl, polyacryl, polyol produced by radical or ring opening polymerization and derivatives thereof; and one or more of the polymers may be used. Preferably, polyvinyl alcohol may be used. The amount of the stabilizer is preferably about 0.01~30 wt % to the weight of the microcapsule dispersed solution. If the amount of the stabilizer is less than 0.01 wt %, the microcapsule may have decreased dispersion stability and if the amount of the stabilizer is more than 30 wt %, the microcapsule may not be produced by gelation of the solution.

The amount of wall-component polymer for the microcapsule containing an active component is about 1~99.99 wt % of the total weight of the microcapsule. If the amount is less than 1%, forming the microcapsule is difficult, and if the amount is more than 99.99%, the active component is not efficiently expressed.

The present invention may be embodied by way of the following examples. However, these examples are provided for the purpose of illustration only, and should not be construed as limiting the scope of the invention.

PREFERRED EMBODIMENT OF THE INVENTION

Example 1

Production of Polycaprolacton Microcapsules Containing Polyethylene Glycol

Each of the polyethylene glycols with molecular weight of 400, 4000, 8000 and 12000 g/mol was mixed with polycaprolacton (Mw 80000 g/mol) at 1:1 ratio in methylene chloride (solvent) and stirred at room temperature to make solution. Each amount of the polyethylene glycol and polycaprolacton was 15 wt % to the methylene chloride. Each of the solution was dissolved into water solution of 1% polyvinyl alcohol (average saponification 89 mol %) and emulsified by mechanical homogenizer at 5000 rpm for 5 min. The concentration of solution of polyethylene glycol/polycaprolacton/methylene chloride is 30 wt % in the aqueous phase. After emulsification, the emulsion was stirred in a vacuum evaporator under reduced-pressure at room temperature to eliminate methylene chloride. The dispersed solution was then filtered to collect capsule. The collected microcapsules were dried in a vacuum dryer at room temperature for one day.

Example 2

Production of polymethyl(meth)acrylate Microcapsules Containing Polyethylene Glycol Each of the polyethylene glycols with molecular weight of 400, 4000, 8000 and 12000 g/mol was mixed with polymethylmethacrylate (Mw 75000 g/mol) at 1:1 ratio in methylene chloride (solvent) and stirred at room temperature to make solution. Each amount of polyethylene glycol and polymethylmethacrylate employed was 20 wt % to the methylene chloride. The following steps were same with those of Example 1 to prepare the polyethylene glycol/polymethylmethacrylate microcapsules.

Example 3

Production of Polystyrene Microcapsules Containing Polyethylene Glycol

Each of the polyethylene glycols with molecular weight of 400, 4000, 8000 and 12000 g/mol was mixed with polystyrene (Mw 100000 g/mol) at 1:1 ratio in methylene chloride and stirred at room temperature. Each amount of polyethylene glycol and polystyrene employed was 20 wt % to the methylene chloride. The following steps were same with those of Example 1 to prepare the polyethylene glycol/polystyrene microcapsules.

Example 4

Production of Polycaprolacton Microcapsules Containing 2 Polyethylene Glycol 400 g/mol of polyethylene glycol as low molecular weight polyol and 8000 g/mol of polyethylene glycol as high molecular weight polyol were mixed at 7:3, 5:5 and 3:7 ratios in polycaprolacton/methylene chloride solution. The sum (weight) of low molecular weight polyol was high molecular weight polyol was same with the weight of polycaprolacton. Each amount of polyethylene glycol and polycaprolacton employed was 20 wt % to the methylene chloride (solvent). The following steps were same with those of Example 1 to prepare the polyethylene glycol/polycaprolacton microcapsules.

Example 5

Production of Polyethylene Glycol/Polycaprolacton Microcapsules Containing Papain Papain was dispersed in 400 g/mol of low molecular polyethylene glycol. The amount of the papain was 1, 3 and 5 wt % to the total weight of the capsule, respectively. The resulting solution was then re-dispersed in a solution of 8000 g/mol of high molecular weight polyethylene glycol and polycaprolacton in methylene chloride. The amounts of the components used in this Example are same with Example 4. The following steps were same with those of Example 1 to prepare the polyethylene glycol/polycaprolacton microcapsules.

Example 6

Production of polymethyl(meth)acrylate Microcapsules Containing Butylene Glycol

Butylene glycol/polymethylmethacrylate microcapsules were prepared in a similar procedure to that described in Example 2 above, except that butylene glycol was used instead of polyethylene glycol. Butylene glycol and polymethylmethacrylate (Mw 75000 g/mol) was mixed at 3:7 ratio in methylene chloride and stirred at room temperature to dissolve. Each of the butylene glycol and polymethylmethacrylate employed were 20 wt % to the methylene chloride. The following steps were same with those of Example 1 to prepare the polyethylene glycol/polymethylmethacrylate microcapsules.

Example 7

Production of Polyethylene Glycol/Polymethacrylate Microcapsules Containing Licorice Licorice with 5 wt % to polymer was dissolved in a mixed solution of polyethylene glycol and methylene chloride. The resulting solution was mixed with polymethyl(meth)acrylate in methylene chloride. The amounts of the components used in this Example are same with those of Example 2. The following steps were same with those of Example 1 to prepare the polyethylene glycol/polymethylmethacrylate microcapsules.

Example 8

Production of Polyethylene Glycol/Polymethacrylate Microcapsules Containing Ascorbic Acid Ascorbic acid with 5 wt % to polymer was dispersed in polyethylene glycol, then the dispersed solution re-dispersed in polymethylmethacrylate in methylene chloride. The amounts of the components used in this Example are same with those of Example 2. The following steps were same with those of Example 1 to prepare the polyethylene glycol/polymethylmethacrylate microcapsules.

Example 9

Production of Polyethylene Glycol/Polymethacrylate Microcapsules Containing Ascorbic Acid and Lipoic Acid Ascorbic acid and lipoic acid with 5 wt % to polymer were dispersed in polyethylene glycol, then the dispersed solution re-dispersed in polymethylmethacrylate in methylene chloride. The amounts of the components used in this Example are same with those of Example 2. The following steps were same with those of Example 1 to prepare the polyethylene glycol/polymethylmethacrylate microcapsules containing ascorbic acid and lipoic acid at the same time.

Experimental Example 1

Analysis of Polyethylene Glycol/Polymer Microcapsules

The structures of polyethylene glycol/polymer microcapsules prepared in Examples 1~3 were observed with optical microscope. As shown in FIG. 1, the polyethylene glycol/polymer microcapsules have an average particle diameter of 5~20 mm and are spherical. Spherical domain of polyethylene glycol is formed inside of the each microcapsule. However, it was found that the introduction volume of the polyethylene glycol depends on the molecular weight. The introduction volume in the microcapsules according to the molecular weight of polyethylene glycol were measured quantitatively with a thin layer chromatography, and the results are shown in Table 1.

TABLE 1

| | Polyethylene glycol introduction volume (%) | | | |
|---|---|---|---|---|
| | 400 g/mol | 4000 g/mol | 8000 g/mol | 12000 g/mol |
| Example 1 | 0 | 0.5 | 14 | 21 |
| Example 2 | 0 | 0.7 | 18 | 20 |
| Example 3 | 0 | 0.3 | 9 | 16 |

As shown in the above Table 1, the introduction volume of polyethylene glycol depended on the molecular weight. As the molecular weight of polyethylene glycol increased, the introduction volume of polyethylene glycol increased because of decreasing polarity. However, the optical microscopic photograph showed that a low molecular weight polyethylene glycol can also form an internal domain. Such formation of the microcapsule and domain happens because the polyethylene glycol forms a specific domain in the microcapsule by phase separation, and then slowly flew out to the external microcapsule during the solvent removal. This behavior of the low molecular weight polyethylene glycol shows that a low molecular weight polyethylene glycol acts as a template to induce formation of an internal domain during the manufacturing process of the microcapsule. It was also found that a high molecular weight polyethylene glycol was loaded in the microcapsule irrespective of the process.

Conventionally, it was difficult to prepare a microcapsule containing licorice with high concentration because the solubility of licorice is limited. The licorice does not absolutely dissolve in organic solvent such as methylene chloride, and does not dissolve more than 2% in polyol at 60° C. or more. However, in Example 7, a microcapsule containing with 10% or more of concentration licorice was prepared by selecting and mixing suitable polyol and organic solvent at room temperature.

Example 8 confirmed that a water-soluble component as well as an oil-soluble component can be capsulized. Although ascorbic acid is easily discolored and unstable in cosmetic compositions, the present invention capsulized ascorbic acid into polymer capsule with a simple method of a polyol/polymer microcapsule.

The microcapsule of Example 9, which collected lipoic acid and ascorbic acid at the same time, confirmed that the microcapsule of the present invention is also able to collect both oil- and water-soluble active components at the same time. The lipoic acid is an oil-soluble component which has an excellent antioxidation effect, and the ascorbic acid is a water-soluble component. Effects of these two active components are maximized when they are used at the same time rather than separately (H. R. Rosenberg, R. Culik, Arch. Biochem. Biophys. 80 (1959) 86-93). However it was not reported that a microcapsule collected two active components at the same time because of the solubility difference between the two active components. The present invention confirmed that it is possible to collect two active components having different solubilities in a single microcapsule by using the manufacturing method of polyol/polymer microcapsules. The amounts of active components in the microcapsules of the above Examples 7~9 were analized with HPLC, and collection ratios of the active components were more than 95%.

Experimental Example 2

Introduction Volume According to Mixing Ratio of Polyethylene Glycol

Figure 2:
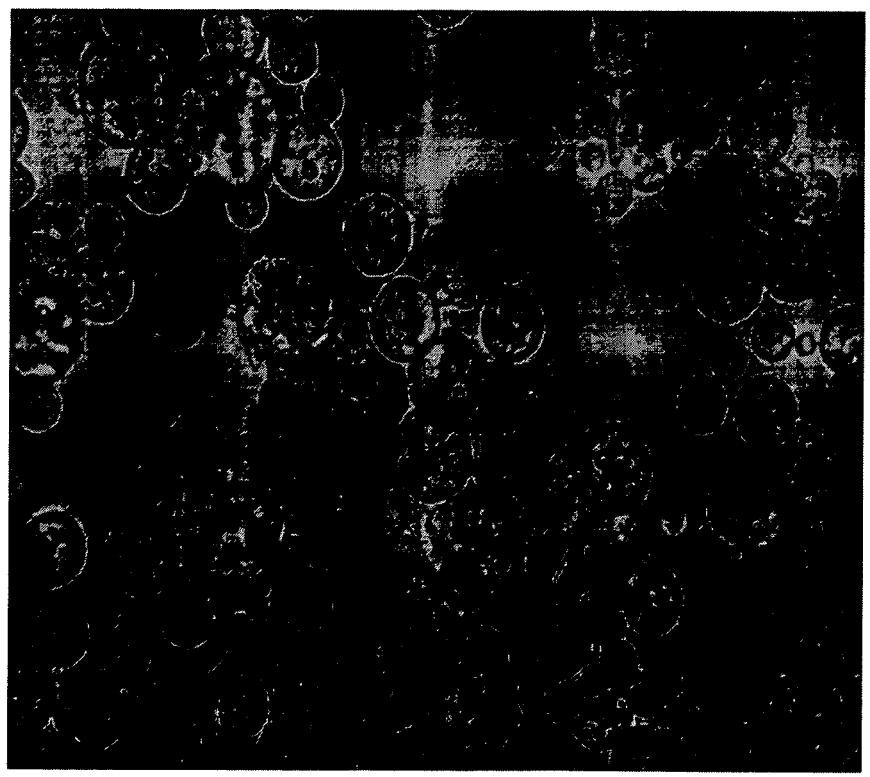
FIG. 2. shows an optical microscopic photograph of polyethyleneglycol/polycaprolactone microcapsules (400 g/mol: 8000 g/mol=5:5 (w/w)).

In order to observe the introduction volume of polyethylene glycol according to the mixing ratio of polyethylene glycol, the polyethylene glycol/polycaprolacton microcapsule produced in Example 4 was quantitatively analized by thin layer chromatography and the result is shown in Table 2. The introduction volume of polyethylene glycol into the microcapsule was found to depend on the mixing ratio of a low and a high molecular weight polyethylene glycol. However, the optical microscopic photograph of FIG. 2 shows that the shape of the microcapsule was independent of the mixing ratio of a low and a high molecular weight polyethylene glycol. This result shows that the low molecular weight polyethylene glycol is just a template for domain forming, and the high molecular weight polyethylene glycol remains in the microcapsule.

TABLE 2

| Mixing ratio | Polyethylene glycol introduction volume (%) | |
| --- | --- | --- |
| 400 g/mol:8000 g/mol | 400 g/mol | 8000 g/mol |
| 10:0 | 0 | 0 |
| 7:3 | 0 | 4 |
| 5:5 | 0 | 6.5 |
| 3:7 | 0 | 9.5 |
| 0:10 | 0 | 14 |

Experimental Example 3

Figure 3:
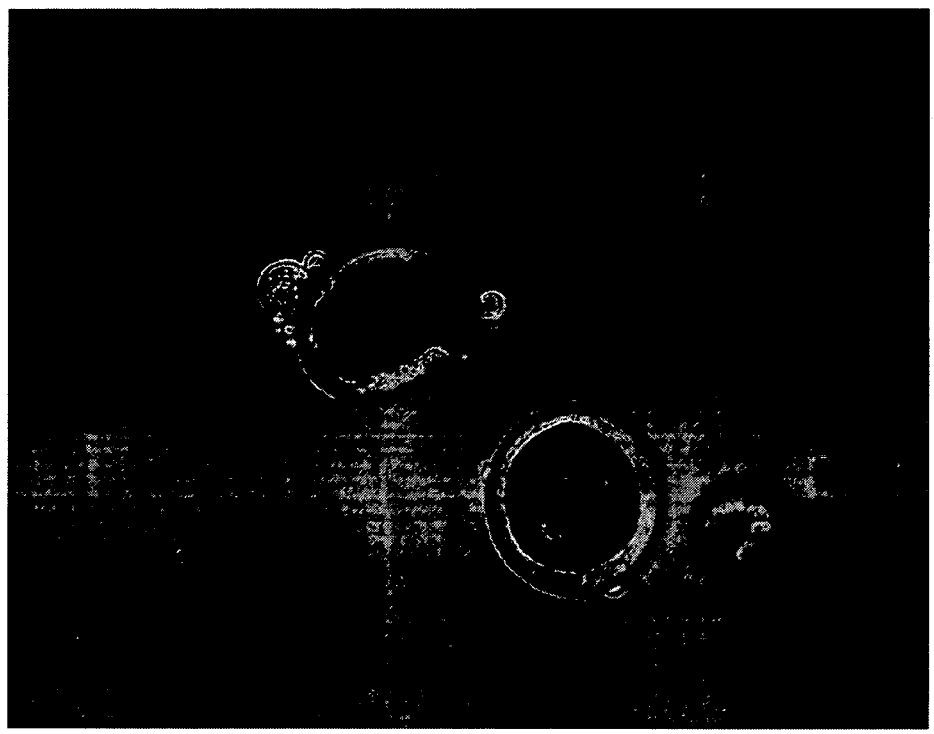
FIG. 3. shows an optical microscopic photograph of polyethyleneglycol/polycaprolactone microcapsules containing papain.
Figure 4:
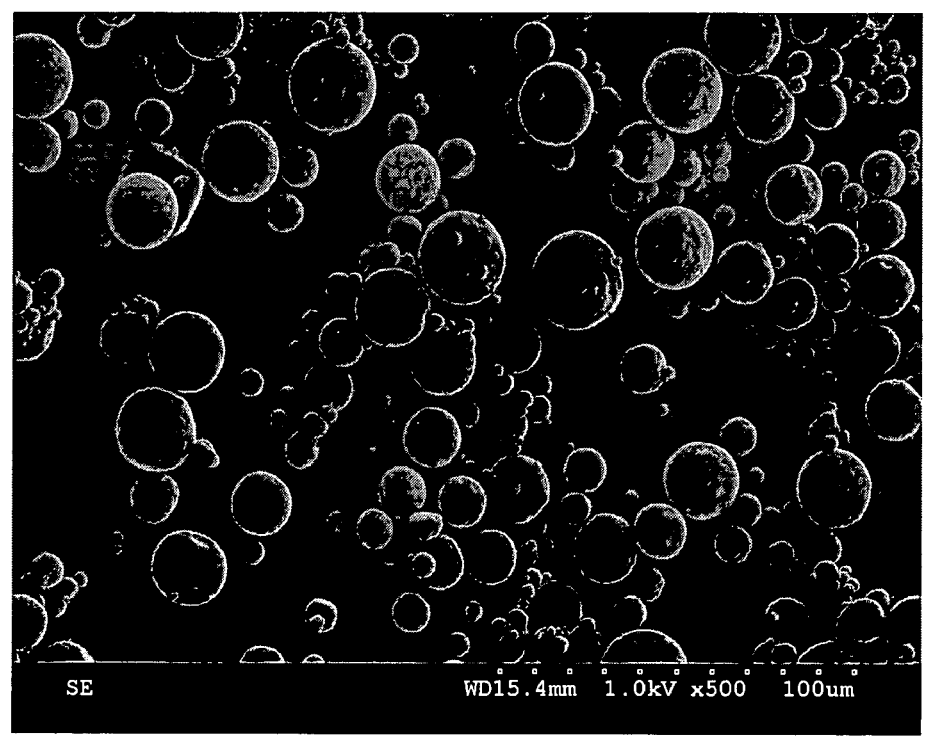
FIG. 4. shows a scanning electron microscopic photograph of polyethyleneglycol/polycaprolactone microcapsules containing papain.

Introduction Volume of Papain in Polyethylene Glycol/Polycaprolacton Microcapsules FIG. 3 shows an optical microscopic photograph of a polyethylene glycol/polycaprolacton containing papain microcapsules prepared in the Example 5. Contrary to FIG. 1, areas of the papain can be easily observed in the microcapsule. FIG. 4 shows a scanning electron microscopic photograph of a polyethylene glycol/polycaprolacton containing papain microcapsules.

The external wall of the microcapsule was formed with smooth polycaprolacton and it was found that papain and polyethylene glycol were efficiently collected within the external wall of polycaprolacton since effluence of papain or polyethylene glycol to the outside of the microcapsule was not observed.

The introduction volume of papain in the microcapsules was analized as follows: 50 ml of the microcapsules containing papain were added into 1 ml of dimethylsulfoxide and incubated for an hour. 2 ml solution of 0.05% sodiumdodecylsulfate/0.01N sodiumhydroxide was added thereto the solution was and held at room temperature for one hour to dissolve polymer and enzyme completely. The resulting solution was then protein analized by Micro-BCA, and the result is shown in Table 3. As shown in Table 3, the method of the present invention is able to efficiently collect enzyme.

TABLE 3

| Papain introduction volume (wt %, calculated value) | Introduction volume of papain (wt %, measured value) | Introduction ratio (%) |
| --- | --- | --- |
| 1 | 0.99 | 99 |
| 3 | 2.79 | 93 |
| 5 | 4.55 | 91 |

Experimental Example 4

Stability of Papain in Polyethylene Glycol/Polycaprolacton Microcapsules

Activities of papain in the polyethylene glycol/polycaprolacton microcapsules prepared in the Example 5 were analyzed according to storage temperature. The activity was measured by using a microcapsule containing 3 wt % of papain.

Activities of papain in the microcapsules were analyzed as follows: 20 ml of microcapsules containing papain was added into 1 ml of acetone and irradiated with ultrasonic waves for 10 seconds, then centrifuged at 12000 rpm for 5 min. This process was repeated three times to obtain pure enzyme. Activity of the pure enzyme was measured with UV spectrophotometer using casein as substrate at 280 nm. Activities of papain according to storage condition are shown in Table 4. Papain in polyethylene glycol/polycaprolacton microcapsules showed excellent activity after long time storage. This excellent activity means that the polyol such as polyethylene glycol efficiently stabilizes enzyme in the microcapsules. In other words, the polyol is suitably located between enzyme and wall-component polymer such as polycaprolacton to provide hydrophobic distribution and block direct interaction of enzyme and polymer, and therefore, to stabilize the enzyme.

TABLE 4

| | Dry state | | Wet state | |
| --- | --- | --- | --- | --- |
| Storage Time | Room Temp. | 40° C. | Room Temp. | 40° C. |
| Immediately after production | 100 | 100 | 100 | 100 |
| After 2 weeks | 97 ± 3 | 92 ± 4 | 93 ± 5 | 89 ± 5 |
| After 4 weeks | 95 ± 4 | 91 ± 2 | 90 ± 3 | 82 ± 4 |

Experimental Example 5

Stability Analysis of Active Component in Microcapsules

In order to confirm the stability of the active component in polyol/polymer microcapsules prepared in the Examples 7~9, the microcapsules were employed to the following Formulation 1~3.

Formulation 1 (a Soluble Formulation)

A soluble formulation as colorless gel was made according to the composition of the Table 5. The viscosity of the soluble formulation is 4,000 cps. The viscosity was measured with Brookfield (LVDVII+) at 30° C., 12 rpm.

TABLE 5

| Component | Content (wt %) |
| --- | --- |
| Glycerin | 5 |
| Propylene glycol | 4 |
| Microcapsules of Examples 7~9 | 5 |
| Ethanol | 10 |
| Sodium polyacrylate | 0.5 |
| Preservative | quantitative |
| Purified water | To 100 |

The prepared samples were stored at 25° C. and 40° C. separately in an oven. After that, the samples were picked and the amount of residual active components measured with liquid chromatography. The result is shown in Table 6. As shown in Table 6, the active components in polyol/polymer microcapsules showed excellent stability in the soluble formulation.

TABLE 6

| | | Initial concentration Maintenance ratio(%) | | | |
| --- | --- | --- | --- | --- | --- |
| Microcapsule | Temp. (° C.) | After 1 week | After 2 weeks | After 4 weeks | After 8 weeks |
| Microcapsule of Example 7 | 25 | 100 | 100 | 100 | 100 |
| | 40 | 100 | 99 | 98 | 97 |
| Microcapsule of Example 8 | 25 | 100 | 98 | 96 | 93 |
| | 40 | 100 | 98 | 94 | 93 |
| Microcapsule of Example 9 | | | | | |
| Lipoic acid | 25 | 100 | 98 | 96 | 93 |
| | 40 | 100 | 97 | 95 | 92 |

TABLE 6-continued

| Microcapsule | Temp. (° C.) | Initial concentration Maintenance ratio(%) | | | |
|---|---|---|---|---|---|
| | | After 1 week | After 2 weeks | After 4 weeks | After 8 weeks |
| Ascorbic acid | 25 | 100 | 97 | 94 | 94 |
| | 40 | 100 | 95 | 92 | 91 |

Formulation 2 (an Emulsion)

In order to observe stability in an emulsion, a lotion was made according to the composition of the Table 7. A lotion as an opaque gel was produced by dissolving the organic phase and aqueous phase completely at 70° C. and emulsifying at 7,000 rpm for 5 min. The viscosity of the lotion was 2,500 cps.

TABLE 7

| Component | Content (wt %) |
|---|---|
| Stearic acid | 2 |
| Cetyl alcohol | 2 |
| Lanolin alcohol | 2 |
| Liquid paraffin | 7 |
| Cyclomethicone | 5 |
| Polyoxyethylene monooleic acid ester | 2 |
| Preservative and antioxidant | quantitative |
| Glycerin | 3 |
| Propylene glycol | 5 |
| Triethylamine | 1 |
| Microcapsules of Examples 7~9 | 8 |
| Sodium polyacrylate | 0.15 |
| Purified water | To 100 |

The prepared samples were stored at 25° C. and 40° C. separately in an oven. After that, the samples were picked and the amount of residual active components measured with liquid chromatography. The result is shown in Table 8. As shown in Table 8, the active components in polyol/polymer microcapsules showed excellent stability in the emulsion.

TABLE 8

| Microcapsule | Temp. (° C.) | Initial concentration Maintenance ratio(%) | | | |
|---|---|---|---|---|---|
| | | After 1 week | After 2 weeks | After 4 weeks | After 8 weeks |
| Microcapsule of Example 7 | 25 | 100 | 100 | 99 | 99 |
| | 40 | 100 | 99 | 98 | 97 |
| Microcapsule of Example 8 | 25 | 100 | 98 | 97 | 97 |
| | 40 | 100 | 98 | 96 | 90 |
| Microcapsule of Example 9 | | | | | |
| Lipoic acid | 25 | 100 | 98 | 98 | 96 |
| | 40 | 100 | 97 | 95 | 92 |
| Ascorbic acid | 25 | 100 | 97 | 95 | 95 |
| | 40 | 100 | 95 | 95 | 89 |

Formulation 3 (a Cream)

In order to observe the stability of the active component collected in polyol/polymer microcapsules (Examples 7~9) in a cream, a cream was made according to the composition of the Table 9.

TABLE 9

| Component | Content (wt %) |
|---|---|
| Bees wax | 2 |
| Stearyl alcohol | 5 |
| Stearic acid | 8 |
| Squalane | 10 |
| Propylene glycol monostearate | 3 |
| Polyoxyethylene cetyl eter | 1 |
| Preservative and antioxidant | quantitative |
| Propylene glycol | 8 |
| Glycerin | 4 |
| Triethylamine | 1 |
| Microcapsules of Examples 7~9 | 2 |
| Purified water | To 100 |

The prepared samples were stored at 25° C. and 40° C. separately in an oven. After that, the samples were picked and the amount of residual active components measured with liquid chromatography. The result is shown in Table 10.

TABLE 10

| Microcapsule | Temp. (° C.) | Initial concentration Maintenance ratio(%) | | | |
|---|---|---|---|---|---|
| | | After 1 week | After 2 weeks | After 4 weeks | After 8 weeks |
| Microcapsule of Example 7 | 25 | 100 | 100 | 100 | 100 |
| | 40 | 100 | 98 | 99 | 92 |
| Microcapsule of Example 8 | 25 | 100 | 100 | 100 | 99 |
| | 40 | 100 | 98 | 98 | 92 |
| Microcapsule of Example 9 | | | | | |
| Lipoic acid | 25 | 100 | 100 | 100 | 94 |
| | 40 | 100 | 97 | 93 | 90 |
| Ascorbic acid | 25 | 100 | 99 | 99 | 95 |
| | 40 | 100 | 92 | 92 | 88 |

As described in the above results, it was confirmed that the active components in polyol/polymer microcapsules according to the present invention had excellent stability in a cosmetic formulations. Accordingly, the active component, which had restricted utility in cosmetic formulation, can be stably used by using the polyol/polymer microcapsule system according to the present invention. In the formulation containing the microcapsules prepared to collect water- and oil-soluble components at the same time in Example 9, it was found that both the water- and the oil-soluble components can to have excellent stability. This excellent stability may be the result that direct contact between the active component and external stimulation are efficiently blocked by the external wall of polymer surrounding the active component.

INDUSTRIAL APPLICABILITY

The polyol/polymer microcapsule according to the present invention is a system that efficiently introduces various active components. The system is able to collect a water-soluble component, an oil-soluble component or oil- and water-soluble components at the same time in the microcapsule. The polyol/polymer microcapsule containing an active component also blocks the effects on the active component of contact with detergent, oil, moisture and air through giving stability to an unstable active component. Owing to the active component not contacting directly the outside but being enclosed within the external wall of polymer, the microcapsule relaxes the stimulation of skin which occurs by direct contact of the active component with the skin.

What is claimed is:

1. A method of preparing triple-layered microcapsules containing an enzyme stabilized therein consisting of the steps of:

1) dispersing an enzyme into a low molecular weight polyol selected from the group consisting of polyethylene glycol, polypropylene glycol, and copolymers or derivatives thereof; butylene glycol, propylene glycol or glycerine, whose molecular weight is 1,000 g/mol or less to form a polyol domain in the microcapsule and stabilize the enzyme;

2) re-dispersing the dispersed enzyme/polyol solution of step 1) into a polymer solution containing high molecular weight polyol selected from the group consisting of polyethylene glycol, polypropylene glycol, and copolymers or derivatives thereof, whose molecular weight is more than 1,000 g/mol to provide hydrophobic distribution of the enzyme in the microcapsule which provides a buffer that prevents direct contact between the enzyme and the hydrophobic wall material in the microcapsule;

3) emulsifying the solution of step 2) to collect an emulsion; and 4) solidifying the enzyme/polyol/polymer emulsion of step 2) and separating the aqueous low molecular weight polyol which flows out from an inner phase through an external surface of the microcapsule while the high molecular polyol remains in the microcapsule and collecting hard polymer microcapsules;

wherein a wall-component polymer selected from the group consisting of poly-L-lactic acid, poly-D,L-glycolic acid, poly-L-lactic acid-co-glycolic acid, poly-D,L-lactic acid-co-glycolic acid, polycaprolactone, polyvalerolactone, polyhydroxybutyrate, polyhydroxyvalerate, polyorthoester, and copolymers produced from these monomers, polystyrene, poly p- or m-methylstyrene, poly p- or m-ethystyrene, poly p- or m-chlorostyrene, poly p- or m-chloromethylstyrene, polystyrene sulfonic acid, poly p-, m- or t-butoxystyrene, polymethyl(meth)acrylate, polyethy(meth)acrylate, polypropyl(meth)acrylate, poly n-butyl(meth)acrylate, polyisobutyl(meth)acrylate, poly t-butyl(meth)acrylate, poly 2-ethylhexyl(meth)acrylate, poly n-octyl(meth)acrylate, polylauryl(meth)acrylate, polystearyl(meth)acrylate, poly 2-hydroxyethyl(meth)acrylate, polyethylene glycol(meth)acrylate, metoxypolyethylene glycol(meth)acrylate, polyglycidyl(meth)acrylate, polydimethylaminoethyl(meth)acrylate, polydiethylaminoethyl(meth)acrylate, polyvinylpropionate, polyvinylbutyrate, polyvinylether, polyallylbutylether, polyallylglycidylether, poly(meth)acrylic acid, polymaleic acid, polyalkyl(meth)acrylamide and poly(meth)acrylonitrile is dissolved in the polymer solution of step 2), thereby producing a three component microcapsule in which the enzyme is surrounded and protected by the high molecular weight polyol and the wall component polymer forms an outer wall around the enzyme and high molecular weight polyol.

2. The method according to claim 1, wherein the enzyme is at least one selected from the group consisting of oxidoreductase, transferase, hydrolase, lyase, isomerase, synthase and ligase.

3. A method of preparing triple-layered microcapsules containing an enzyme stabilized therein consisting of the steps of:

1) dispersing an enzyme into a low molecular weight polyol selected from the group consisting of polyethylene glycol, polypropylene glycol, and copolymers or derivatives thereof butylene glycol, propylene glycol or glycerine, whose molecular weight is 1,000 g/mol or less to form spherical dispersoids in which only the external layer of the enzyme partially dissolves therein to form an enzyme/polyol mixture phase dispersed solution to disperse, protect and stabilize the enzyme;

2) re-dispersing the dispersed enzyme/polyol solution of step 1) into a polymer solution containing high molecular weight polyol selected from the group consisting of polyethylene glycol, polypropylene glycol, and copolymers or derivatives thereof, whose molecular weight is more than 1,000 g/mol to provide hydrophobic distribution of the enzyme in the microcapsule which provides a buffer that prevents direct contact between the enzyme and the hydrophobic wall material in the microcapsule;

3) emulsifying the solution of step 2) to collect an emulsion; and 4) solidifying the enzyme/polyol/polymer emulsion of step 2) and separating the aqueous low molecular weight polyol which flows out from an inner phase through an external surface of the microcapsule while the high molecular polyol remains in the microcapsule and collecting hard polymer microcapsules;

wherein a wall-component polymer selected from the group consisting of poly-L-lactic acid, poly-D,L-glycolic acid, poly-L-lactic acid-co-glycolic acid, poly-D,L-lactic acid-co-glycolic acid, polycaprolactone, polyvalerolactone, polyhydroxybutyrate, polyhydroxyvalerate, polyorthoester, and copolymers produced from these monomers, polystyrene, poly p- or m-methylstyrene, poly p- or m-ethystyrene, poly p- or m-chlorostyrene, poly p- or m-chloromethylstyrene, polystyrene sulfonic acid, poly p-, m- or t-butoxystyrene, polymethyl(meth)acrylate, polyethy(meth)acrylate, polypropyl(meth)acrylate, poly n-butyl(meth)acrylate, polyisobutyl(meth)acrylate, poly t-butyl(meth)acrylate, poly 2-ethylhexyl(meth)acrylate, poly n-octyl(meth)acrylate, polylauryl(meth)acrylate, polystearyl(meth)acrylate, poly 2-hydroxyethyl(meth)acrylate, polyethylene glycol(meth)acrylate, metoxypolyethylene glycol(meth)acrylate, polyglycidyl(meth)acrylate, polydimethylaminoethyl(meth)acrylate, polydiethylaminoethyl(meth)acrylate, polyvinyipropionate, polyvinylbutyrate, polyvinylether, polyallylbutylether, polyallylglycidylether, poly(meth)acrylic acid, polymaleic acid, polyalkyl(meth)acrylamide and poly(meth)acrylonitrile is dissolved in the polymer solution of step 2), thereby producing a three component microcapsule in which the enzyme is surrounded and protected by the high molecular weight polyol and the wall component polymer forms an outer wall around the enzyme and high molecular weight polyol.

4. The method according to claim 3, wherein the enzyme is at least one selected from the group consisting of oxidoreductase, transferase, hydrolase, lyase, isomerase, synthase and ligase.

* * * * *